(12) United States Patent
Que et al.

(10) Patent No.: US 10,260,995 B2
(45) Date of Patent: Apr. 16, 2019

(54) TEST DEVICE OF UNIVERSAL NAIL/SCREW HOLDING POWER

(71) Applicants: NANJING FORESTRY UNIVERSITY, Nanjing, Jiangsu (CN); ZHENGZHOU UNIVERSITY, Zhengzhou, Henan (CN)

(72) Inventors: Zeli Que, Nanjing (CN); Xiaolin Yang, Zhengzhou (CN); Qicheng Teng, Nanjing (CN); Hongyi Lu, Zhengzhou (CN); Feibin Wang, Nanjing (CN); Zherui Li, Nanjing (CN); Weizhen Cai, Nanjing (CN)

(73) Assignees: NANJING FORESTRY UNIVERSITY, Nanjing, Jiangsu (CN); ZHENGZHOU UNIVERSITY, Zhengzhou, Henan (CN)

( * ) Notice: Subject to any disclaimer, the term of this patent is extended or adjusted under 35 U.S.C. 154(b) by 0 days.

(21) Appl. No.: 15/807,452

(22) Filed: Nov. 8, 2017

(65) Prior Publication Data
US 2019/0003926 A1 Jan. 3, 2019

(30) Foreign Application Priority Data
Jun. 28, 2017 (CN) .......................... 2017 1 0510447

(51) Int. Cl.
*G01M 99/00* (2011.01)
*G01N 3/08* (2006.01)
*G01L 5/24* (2006.01)

(52) U.S. Cl.
CPC .............. *G01M 99/00* (2013.01); *G01N 3/08* (2013.01); *G01L 5/24* (2013.01); *G01N 2203/0016* (2013.01)

(58) Field of Classification Search
CPC ........ G01N 3/04; G01N 3/08; G01N 2203/04; G01L 5/24; G01M 99/00
USPC .................................. 73/760, 856, 859, 860
See application file for complete search history.

(56) References Cited

U.S. PATENT DOCUMENTS

| 2,957,342 A | * | 10/1960 | Hanneman ............ G01L 5/0042 73/1.15 |
| 4,662,227 A | * | 5/1987 | Peterson .................. G01N 3/00 73/826 |
| 4,753,115 A | * | 6/1988 | Moody ..................... G01N 3/08 73/826 |

* cited by examiner

*Primary Examiner* — Benjamin R Schmitt
(74) *Attorney, Agent, or Firm* — Li & Cai Intellectual Property (USA) Office

(57) ABSTRACT

A test device of universal nail/screw holding power is provided. The device is capable of penetrating a nail/screw into a test piece at any angle and positioning the test piece on which a nail/screw is penetrated at any angle to test the nail/screw holding power. The device includes a base, two opposite supporting plates, two coaxial disks, an upper bearing plate, a lower bearing plate, a side bearing plate, a through groove, a trapezoid slot, and a plurality of trapezoid bolts on the same circumference. When the disk is turned, at least one trapezoid bolt is inserted into the trapezoid slot; when the at least one trapezoid bolt engages with the trapezoid slot and then is tightened up, the at least one trapezoid bolt and the trapezoid slot cooperatively limit the turn of the disk.

8 Claims, 11 Drawing Sheets

TEST DEVICE OF UNIVERSAL NAIL/SCREW HOLDING POWER

BACKGROUND

1. Technical Field

The present disclosure relates to a test device of universal nail/screw holding power.

2. Description of Related Art

For the sake of testing the nail/screw holding power of test materials, test devices of nail/screw holding power are generally used to hold the nail/screw head through the nail/screw holder to pull upwards the nail that is vertically penetrated into a surface of a test piece, and a ratio of the maximum power necessary for pulling the nail/screw out of the test piece and the penetration length of nail/screw being penetrated into the test piece is served as the nail/screw holding power of the test piece.

If the nail which has not been vertically penetrated into the surface of the test piece, testing the nail/screw holding power would become difficult as the test piece cannot be held firmly.

In addition, for penetrating a nail/screw into a test piece, when vertical to a surface of a test piece, the nail/screw is easy to be penetrated; however, when there is an inclined angle (not a vertical angle) between a nail/screw and a surface of a test piece to be nailed, the nail/screw is difficult to be penetrated by using conventional test devices of nail/screw holding power.

SUMMARY

The primary purpose of the present disclosure is to provide a test device of universal nail/screw holding power which is not only capable of penetrating a nail/screw into a test piece at any angle, but also positioning the test piece on which a nail/screw is penetrated at any angle to test the nail holding power.

According to one exemplary embodiment of the present disclosure, a test device of universal nail/screw holding power is provided, which includes a base on which two opposite supporting plates are disposed, two coaxial disks that are respectively disposed on the two supporting plates, an upper bearing plate, a lower bearing plate, a side bearing plate located at one side of the upper bearing plate and the lower bearing plate are provided between the two disks, a through groove through which a nail can pass is provided on the upper bearing plate, a trapezoid slot which is concentric with the disk is provided on at least one supporting plate, and a plurality of trapezoid bolts are disposed along the same circumference on at least one disk. When the disk is turned, at least one trapezoid bolt is inserted into the trapezoid slot, and when the at least one trapezoid bolt engages with the trapezoid slot and then is tightened up, the at least one trapezoid bolt and the trapezoid slot cooperatively limit the turn of the disk.

The present disclosure has the technical effectiveness characterized in that, in the test device of universal nail/screw holding power, the upper bearing plate, the lower bearing plate and the side bearing plate together form a three-side bearing structure having opening at one side.

When penetrating a nail/screw into a test piece, the test piece, such as wood, is placed between the upper bearing plate and the lower bearing plate through the opening side. The bottom surface of the test piece is in contact with the lower bearing plate, and it is preferably to contact a side of the test piece with the side bearing plate. The disk is turned based on a desired angle of a nail/screw being penetrated into the test piece until the nail/screw penetrated into the test piece is kept vertically. The trapezoid bolt is tightened up and the disk is fixed on the bearing plate to avoid the disk and the test piece turning. The lower bearing plate can stably bear the test piece (it is preferably to use both the lower bearing plate and the side bearing plate to bear the test piece), and then the upright nail/screw passes through the through groove disposed on the upper bearing plate and is vertically penetrated into an upper surface of the test piece. Alternatively, the disk is turned until an upper surface of the test piece is parallel to the horizontal plane, then the trapezoid bolt is tightened up to fix the disk and the test piece, the lower bearing plate stably bears the test piece (it is preferably to use both the lower bearing plate and the side bearing plate to bear the test piece), and the nail/screw which forms a certain angle with the horizontal plane is penetrated into the upper surface of the test piece.

When testing the nail/screw holding power of the test piece, the upper surface of the test piece on which the nail/screw has been penetrated is in contact with the bottom of the upper bearing plate, and the nail/screw passes through the through groove disposed on the upper bearing plate. Then, the disk is turned until the nail/screw on the test piece is in a vertically upward direction, the side of the test piece is in contact with the side bearing plate, and the upper and side bearing plate together bear the test piece. Afterwards, the trapezoid bolt is tightened up to avoid the disk and the test piece turning, so that the nail/screw can be pulled out upwards. The test device of universal nail/screw holding power provided by the present disclosure is capable of testing the nail/screw holding power of a nail/screw being penetrated at any angle. In addition, the present disclosure is simple in structure and convenient to use.

The test device of universal nail/screw holding power provided by the present disclosure includes a penetrating guiding apparatus which includes a left bottom plate disposed on the top surface of the upper bearing plate, a left guiding plate rotatably connected with the left bottom plate through a left turning shaft, a right guiding plate rotatably connected with a right bottom plate through a right turning shaft, in which the left turning shaft and the right turning shaft are parallel to each other and the left guiding plate and the right guiding plate are relative to each other; a nailing groove formed on a relative surface of the left guiding plate and the right guiding plate, and the penetrate groove communicated with the through groove; the right bottom plate slidably connected with the left bottom plate in a direction vertical to the right turning shaft; a position giving slot, which extends in a direction vertical to the left turning shaft, disposed on the left guiding plate, and a connecting blot, which passes through the position giving slot, connected with the right guiding plate through screw threads; when turning the connecting bolt, the right bottom plate being pushed to slide with respect to the left bottom plate so as to change a distance between the left guiding plate and the right guiding plate; a turning angle fixed plate, which is vertical to the left turning shaft, fixed on the left bottom plate, and an arc-shaped turning guiding slot, which is coaxial with the left turning shaft, disposed on the turning angle fixed plate, and a turning angle adjusting blot passing through the turning guiding slot to connect to the left guiding plate.

The present disclosure employs the penetrating guiding apparatus to resolve the technical problem concerning that when applying an action force to a nail/screw, the nail/screw is prone to incline and thus difficult to be penetrated in accordance with a determined angle; especially when a nail/screw is penetrated into an uneven surface. When operating the penetrating guiding apparatus provided by the present disclosure, the left guiding plate is turned to enable the left guiding plate to turn (overturn) by taking the left turning shaft as the center to a desired angle, and the turning angle adjusting bolt is tightened up to avoid the left guiding plate turning. Then the right guiding plate is turned to enable the right guide plate to turn (overturn) by taking the right turning shaft as the center to an angle parallel to the left guiding plate. Meanwhile, the connecting bolt is turned and the right bottom plate slides with respect to the left bottom plate to change the distance between the left guiding plate and the right guiding plate, so that the gap between the bottom surface of the nailing groove of the left guiding plate and the bottom surface of the nailing groove of the right guiding plate is substantially the same as the diameter of the nail/screw. After that, the connecting bolt is tightened up again, and the nail/screw passes through the nailing groove and the through groove disposed on the upper bearing plate. Through such a manner, the nail/screw is guided by the bottom surface of the nailing groove, so when applying an action force to penetrate the nail/screw into a test piece, the nail/screw is certainly guided to penetrate into the test piece through the nailing groove.

As the bottom surface of the nailing groove of the left guiding plate and the bottom surface of the nailing groove of the right guiding plate can merely guide a nail/screw in the left-and-right direction, the present disclosure further provides the following technical solution to enable a nail/screw to be guided in the front-and-rear direction.

In the test device of universal nail/screw holding power, the front and rear sides of an upper portion of the nailing groove are inclined planes and the width of the upper portion of the nailing groove is wide at top and narrow at bottom in the front-and-rear direction. Two sliding blocks are oppositely and slidably disposed at the front and rear sides of the nailing groove. A front sliding slot and a rear sliding slot which are parallel to the front and rear sides of the nailing groove are respectively disposed on the left guiding plate and the right guiding plate. A front sliding rod and a rear sliding rod pass through the front sliding block, the front sliding slot, the rear sliding block and the rear sliding slot, respectively. The front sliding rod axially passes through a fore-and-aft gap controlling plate, the rear sliding rod axially passes through a lateral guiding slot disposed on the fore-and-aft gap controlling plate, and the lateral guiding slot parallelly extends along the axis of the left turning shaft. When the front sliding rod slides in the front sliding slot and the rear sliding rod slides in the rear sliding slot and the lateral guiding slot, a gap between the front sliding block and the rear sliding block changes.

When operating, the distance between the bottom surface of the nailing groove of the left guiding plate and the bottom surface of the nailing groove of the right guiding plate is adjusted to be substantially the same as the diameter of the nail/screw, and the front sliding rod is adjusted to move in the front sliding slot to change the position of the front sliding block. Meanwhile, the rear sliding rod is adjusted to move in the rear sliding groove and the lateral guiding slot to change the position of the rear sliding block. Because the front sliding block and the rear sliding block are both slidably disposed on the inclined front side and the inclined rear side of the nailing groove, when the position of the front sliding block changes, the gap between the front sliding block and the rear sliding block changes. When the gap between the front sliding block and the rear sliding block is also adjusted to be substantially the same as the diameter of the nail/screw, the connecting bolt is tightened up, so that the nail/screw passes through a space cooperatively defined by the front sliding block, the rear sliding block, the bottom surface of the nailing groove of the left bottom plate and the bottom surface of the nailing groove of the right bottom plate, and then passes through the through groove disposed on the upper bearing plate to be penetrated into the test piece placed on the lower bearing plate. By using this manner, when the nail/screw is penetrated into the test piece, the nail/screw is guided by the bottom surfaces of the two nailing grooves in the left-and-right direction while being guided by the front sliding block and the rear sliding block in the front-and-rear direction, so that the guiding function can be performed more stably and accurately, thereby ensuring the penetrating directionality.

In the test device of universal nail/screw holding power, a lower protrusion protruding downwards is provided at the bottom of the right bottom plate, and the lower protrusion is slidably cooperated with a guiding groove disposed on the upper bearing plate in a direction vertical to the right turning shaft. By virtue of the manner, when the right bottom plate moves with respect to the left bottom plate, the guiding groove can perform the guiding function toward the lower protrusion at the front-and-rear position, thereby making the moving direction of the right bottom plate more accurate, so as to increase the smoothness.

In the test device of universal nail/screw holding power, a side protrusion extending forwards and backwards is respectively disposed at the front side and the rear side of the right bottom plate, and the side protrusion is slidably cooperated with a guiding sliding track disposed on the left bottom plate in a direction vertical to the right turning shaft. By virtue of the manner, when the right bottom plate moves with respect to the left bottom plate, the guiding sliding track can perform the guiding function toward the side protrusion at the upper-and-lower position, thereby making the moving direction of the right bottom plate more accurate, so as to increase the smoothness.

In the test device of universal nail/screw holding power, the turning angle fixed plate has graduation reflecting the turning angle of the left guiding plate, so that the turning angle of the left guiding plate can be directly observed.

In the test device of universal nail/screw holding power, a plurality of connecting rods parallel to the axis of the disk are provided between the two disks, and the upper bearing plate, the lower bearing plate and the side bearing plate are fixed on the connecting rods.

In the test device of universal nail/screw holding power, the two supporting plates are movably connected to the base in a direction parallel to the axis of the disk with respect to the base, so that a relative distance between the two supporting plates can be adjusted.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

Figure 1:
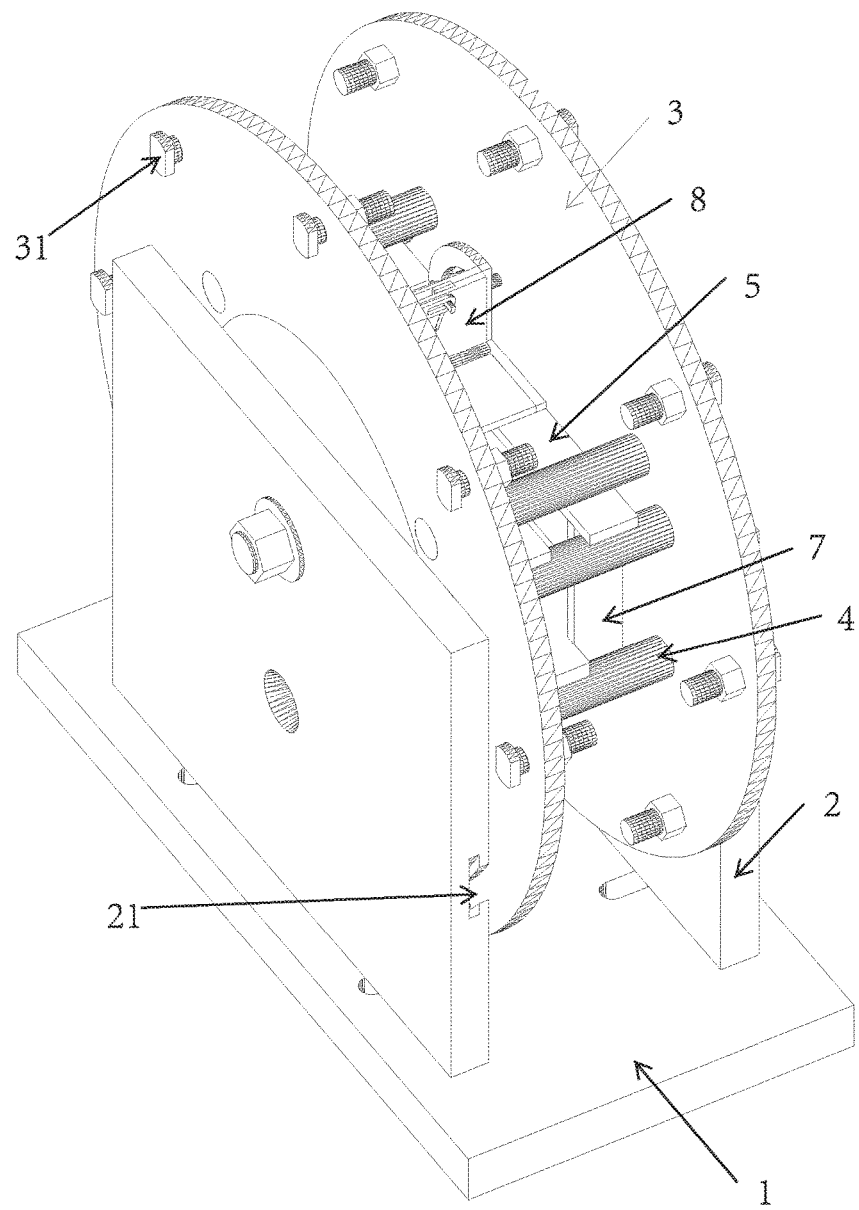
FIG. 1 is a schematic diagram of a test device of universal nail/screw holding power according to the present disclosure.

As shown in the figures, a base 1, a sliding slot 11, a supporting plate 2, a trapezoid slot 21, a disk 3, a trapezoid bolt 31, a connecting rod 4, an upper bearing plate 5, a through groove 51, a positioning groove 52, a guiding groove 53, a lower bearing plate 6, a side bearing plate 7, a penetrating guiding apparatus 8, a left bottom plate 81, a left turning shaft 83, a left guiding plate 85, a left nailing groove 87, a positioning platform 89, a guiding sliding track 91, a position giving slot 93, a left front sliding block 95, a left rear sliding block 97, a left front sliding slot 99, a left rear sliding slot 101, a front sliding rod 103, a left side fore-and-aft gap controlling plate 105, a right bottom plate 82, a right turning shaft 84, a right guiding plate 86, a right nailing groove 88, a lower protrusion 90, a side protrusion 92, a connecting bolt 94, a right front sliding block 96, a right rear sliding block 98, a right front sliding slot 100, a right rear sliding slot 102, a rear sliding rod 104, a right side fore-and-aft gap controlling plate 106, a lateral guiding slot 200, a turning angle fixed plate 201, a turning guiding slot 202, a turning angle adjusting blot 203, a nail/screw 300 and a test piece 400 are provided.

DESCRIPTION OF THE EXEMPLARY EMBODIMENTS

Reference will now be made in detail to the exemplary embodiments of the present disclosure, examples of which are illustrated in the accompanying drawings. Wherever possible, the same reference numbers are used in the drawings and the description to refer to the same or like parts.

Figure 2:
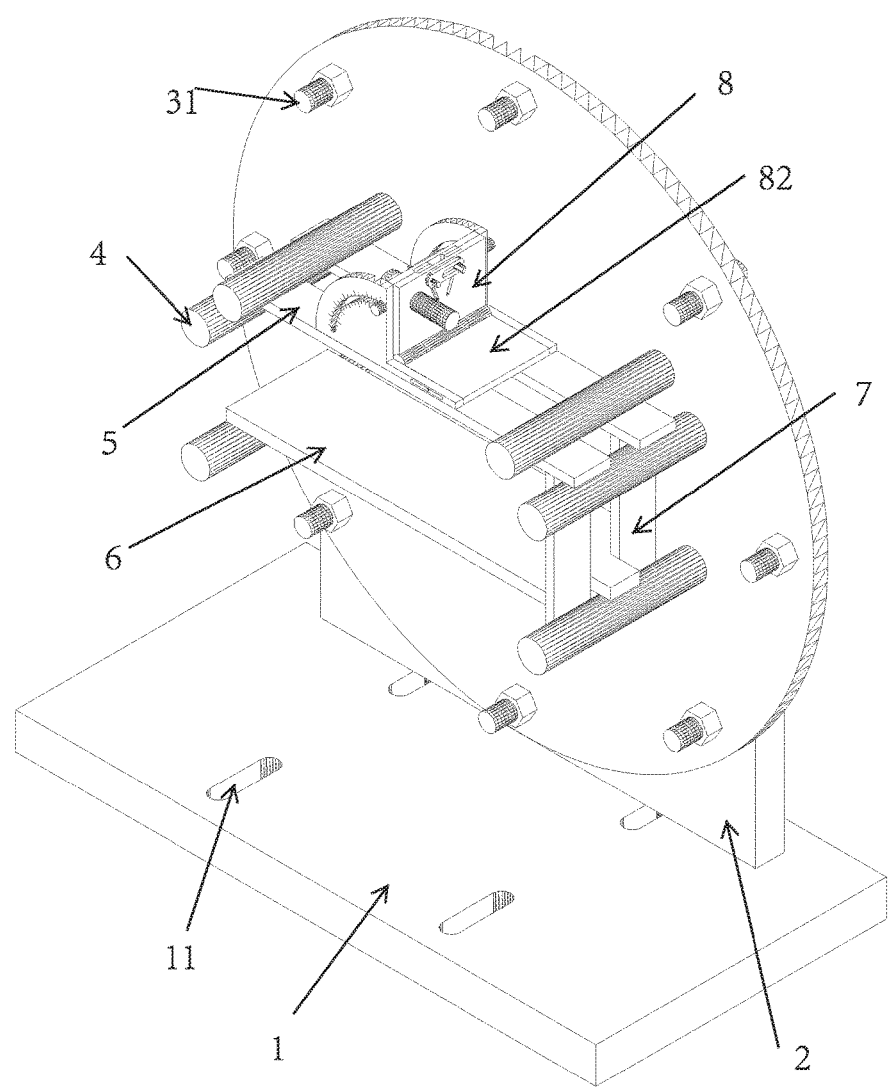
FIG. 2 is a schematic diagram of a test device of universal nail/screw holding power according to the present disclosure, in which one supporting plate and one disk are omitted.
Figure 3:
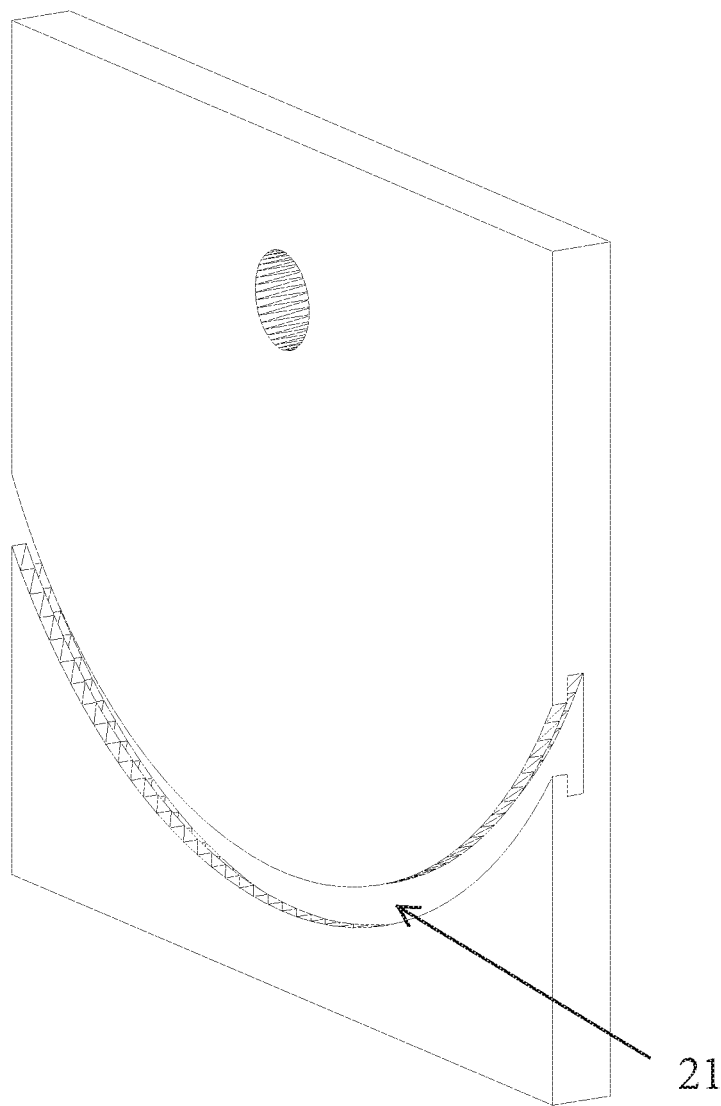
FIG. 3 is a schematic diagram of a supporting plate according to the present disclosure.
Figure 4:
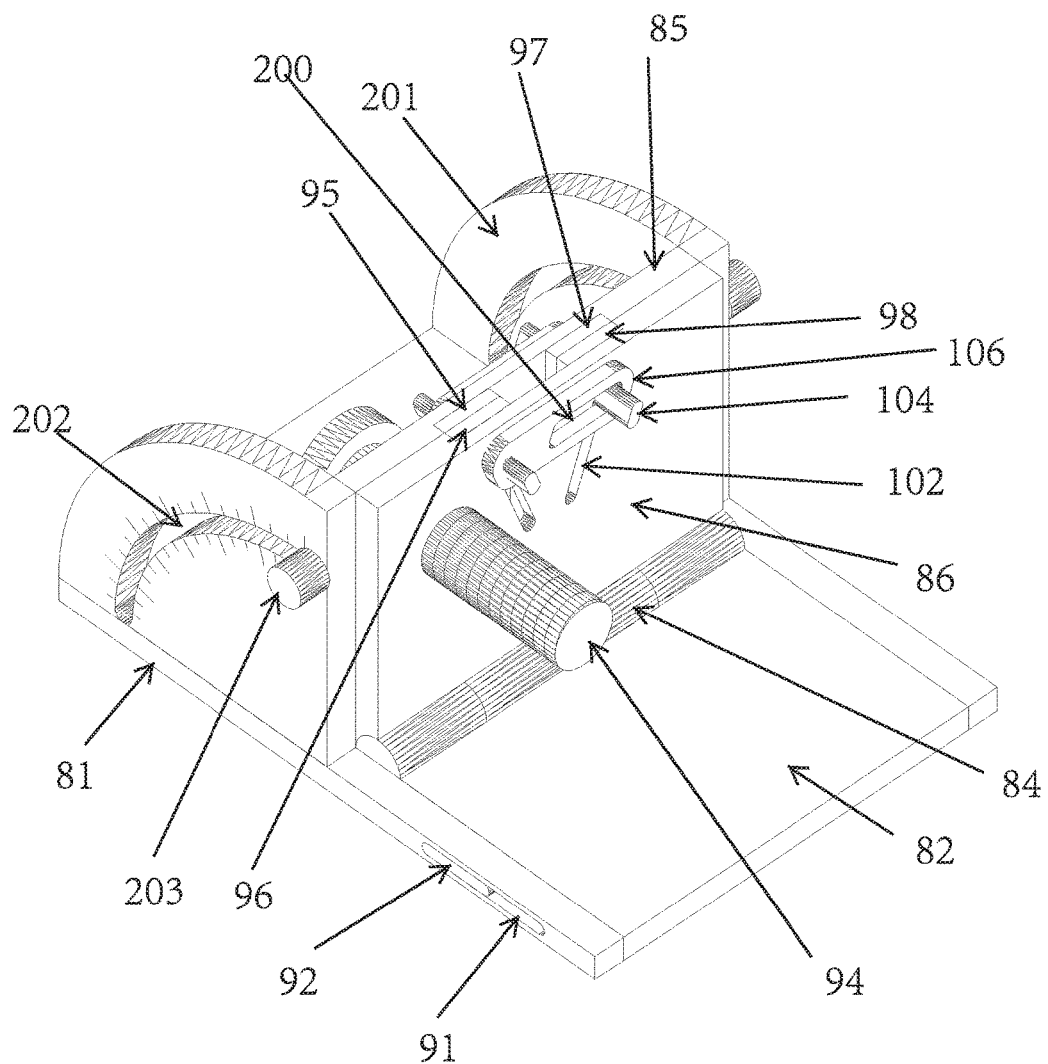
FIG. 4 is a schematic diagram of a penetrating guiding apparatus according to the present disclosure.
Figure 5:
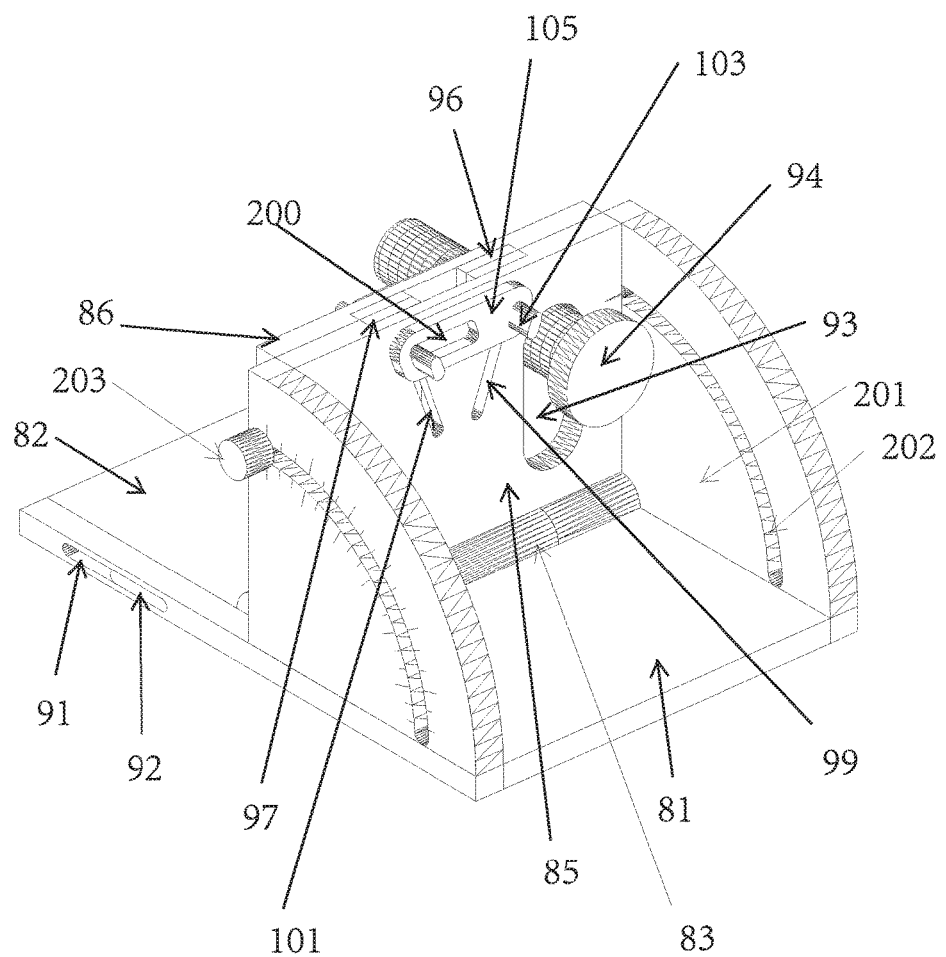
FIG. 5 is another diagram of a penetrating guiding apparatus according to the present disclosure.
Figure 6:
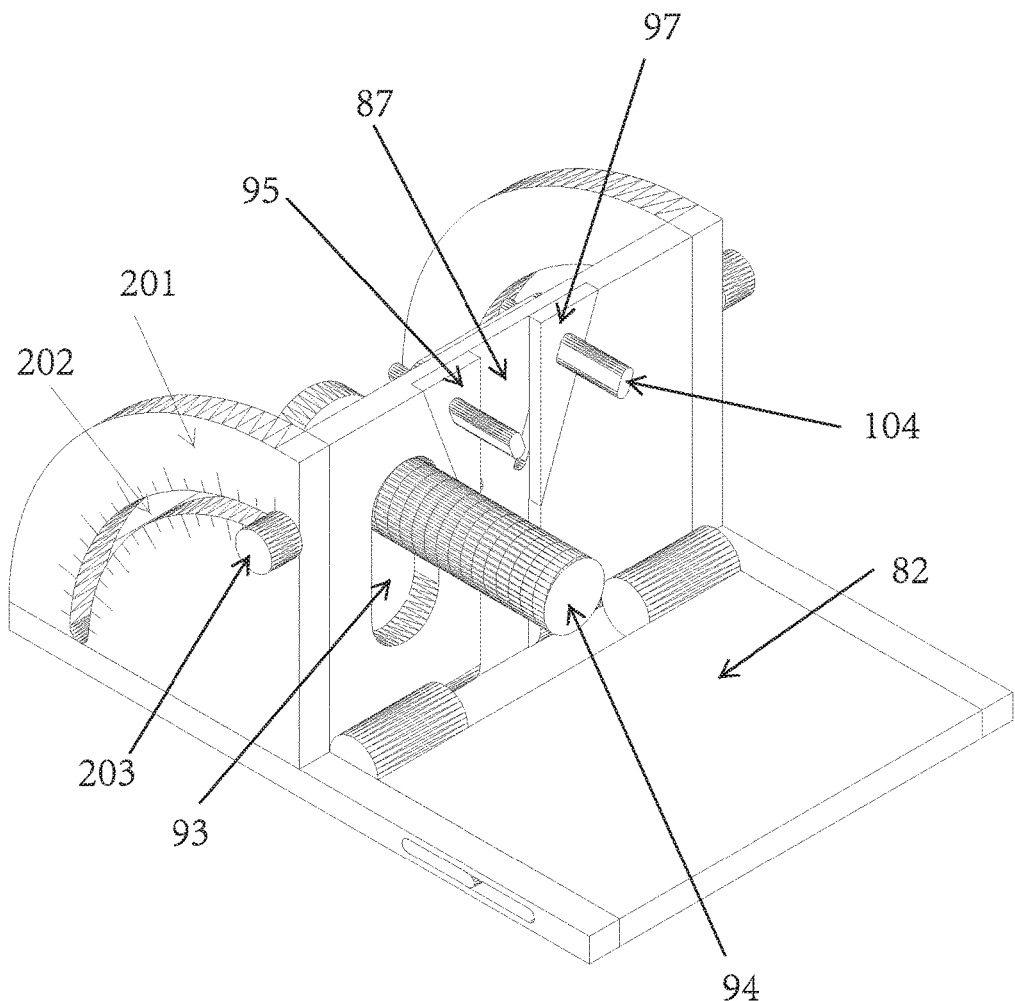
FIG. 6 is a schematic diagram of a penetrating guiding apparatus according to the present disclosure, in which a right guiding plate is omitted.
Figure 7:
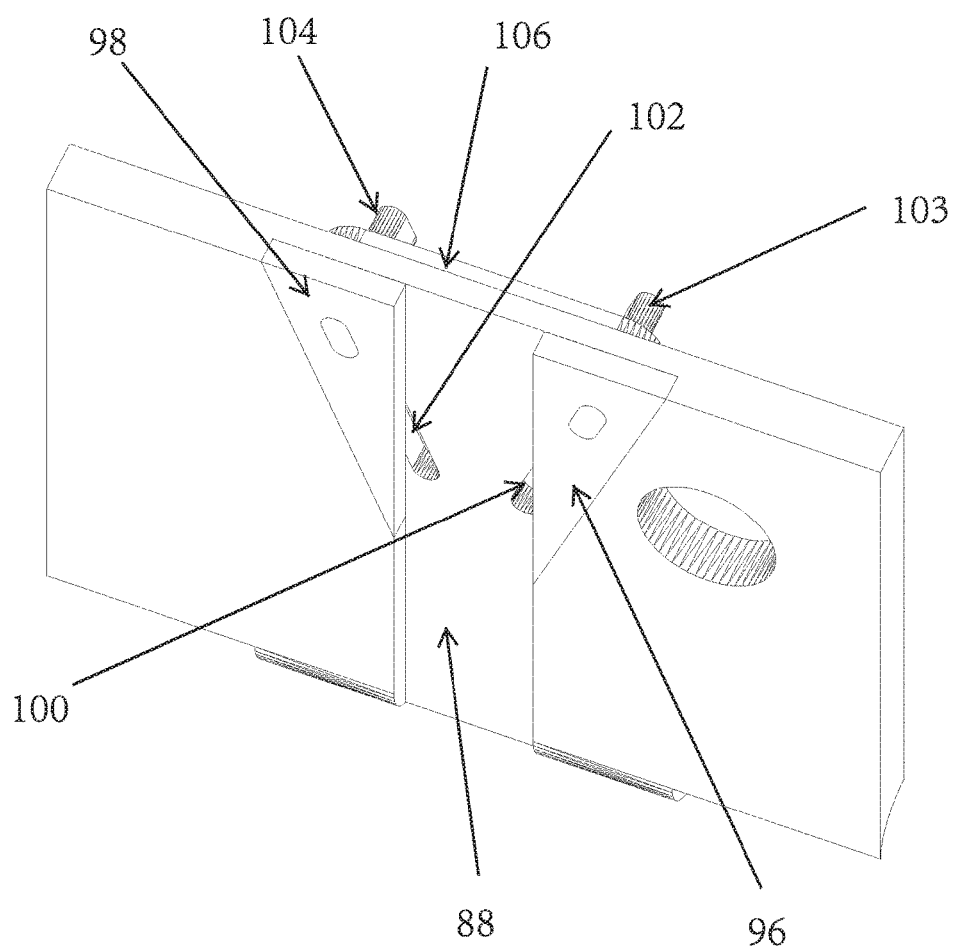
FIG. 7 is a schematic diagram of a right guiding plate, a right front sliding block and a right rear sliding block according to the present disclosure.

Reference is made to FIG. 1 and FIG. 2. A base 1 on which two opposite guiding plates 2 are disposed is provided. Two disks 3 which are coaxial are rotatably disposed on the two supporting plates 2, respectively. A plurality of connecting rods 4 which are parallel to each other are disposed between the two disks 3.

A sliding slot 11 which is parallel to the axis of the disk 3 is disposed on the base 1. A fixed blot passes through the sliding slot 11 to connect with the lower portion of the supporting plate 2. When the fixed bolt is loosened, and the two supporting plates 2 are movable in the direction parallel to the axis of the disk 3 with respect to the base 1.

An upper bearing plate 5, a lower bearing plate 6 and a side bearing plate 7 are respectively fixed on the plurality of connecting rods 4. The side bearing plate 7 is located at one side of the upper bearing plate 5 and the lower bearing plate 6. The upper bearing plate 5 is provided with a through groove 51 through which a nail/screw can pass.

A plurality of trapezoid bolts 31 are disposed along the same circumference in each disk 3, and a trapezoid slot 21 which is concentric with the disk 3 is provided at an internal side of each supporting plate 2. When the disk 3 is turned, at least one trapezoid bolt 31 is inserted into the trapezoid slot 21; when the at least one trapezoid bolt 31 engages with the trapezoid slot 21 and then is tightened up, the at least one trapezoid bolt 31 and the trapezoid slot 21 cooperatively limit the turn of the disk 3.

Reference is made to FIG. 4 to FIG. 7. A penetrating guiding apparatus 8 includes a left bottom plate 81 disposed on the upper bearing plate 5, a left guiding plate 85 rotatably connected with the left bottom plate 81 through a left turning shaft 83, a right guiding plate 86 rotatably connected with a right bottom plate 82 through a right turning shaft 84, in which the left turning shaft 83 and the right turning shaft 84 are parallel to each other and the left guiding plate 85 and the right guiding plate 86 are relative to each other. A nailing groove, which is formed by a left nailing groove 87 and a right nailing groove 88, is formed on a relative surface of the left guiding plate 85 and the right guiding plate 86. The nailing groove is communicated with a through groove 51.

A positioning platform 89 protruding downwards is provided at the bottom of the left bottom plate 81, and the positioning platform 89 cooperates with a positioning groove 52 disposed on the upper bearing plate 5 to prevent the left bottom plate 81 from moving in all-around direction with respect to the upper bearing plate 5. The positioning platform 89 can be pulled out of the positioning groove 52. A lower protrusion 90 protruding downwards is provided at the bottom of the right bottom plate 82, and the lower protrusion 90 is slidably cooperated with a guiding groove 53 disposed on the upper bearing plate 5 in a direction vertical to the right turning shaft 84. A side protrusion 92 extending forwards and backwards is respectively disposed at the front and rear sides of the right bottom plate 82, and the side protrusion 92 is slidably cooperated with a guiding sliding track 91 disposed on the left bottom plate 81 in a direction vertical to the right turning shaft 84.

A position giving slot 93, which extends in a direction vertical to the left turning shaft 83, is disposed on the left guiding plate 85. A connecting bolt 94, which passes through the position giving slot 93, is connected with the right guiding plate 86 through screw threads. When turning the connecting bolt 94, the left guiding plate 85 and the right guiding plate 86 are turned to be parallel to each other and the right bottom plate 82 is pushed to move with respect to the left bottom plate 81 to change a distance between the left guiding plate 85 and the right guiding plate 86 which are relative and parallel to each other, so as to change a gap between the bottom surface of the left nailing groove 87 and the bottom surface of the right nailing groove 88.

The front and rear sides of an upper portion of the left nailing groove 87 are inclined planes and the width of the upper portion of the left nailing groove 87 is wide at top and narrow at bottom in the front-and-rear direction. A left front sliding block 95 and a left rear sliding block 97 are oppositely and slidably disposed at the front and rear sides of the left nailing groove 87. A left front sliding slot 99 and a left rear sliding slot 101 which are parallel to the front and rear sides of the left nailing groove 87 are disposed on the left guiding plate 85. The right nailing groove 88, a right front sliding block 96, a right rear sliding block 98, a right front sliding slot 100 and a right rear sliding slot 102 are respectively symmetrical to the left nailing groove 87, the left front sliding block 95, the left rear sliding block 97, the left front sliding slot 99 and the left rear sliding slot 101. For sake of brevity, the details are omitted.

A front sliding rod 103 passes through the left front sliding block 95, the right front sliding block 96, the left front sliding slot 99, the right front sliding slot 100, a left side fore-and-aft gap controlling plate 105, and a right side fore-and-aft gap controlling plate 106. A rear sliding rod 104 passes through the left rear sliding block 97, the right rear sliding block 98, the left rear sliding slot 101 and the right rear sliding slot 102, and passes through a lateral guiding slot 200 between the left side fore-and-aft gap controlling plate 105 and the right side fore-and-aft gap controlling plate 106, in which the lateral guiding slot 200 parallelly extends along the axis of the left turning shaft 83. When the front sliding rod 103 slides in the left front sliding slot 99 and the right front sliding slot 100, the left front sliding block 95 and the right front sliding block 96 are driven to respectively move along the front side of the upper portion of the left nailing groove 87 and the front side of the upper portion of the right nailing groove 88. When the rear sliding rod 104 slides in the left rear sliding slot 101 and the right rear sliding slot 102 and slides in the lateral guiding slot 200 simultaneously, the left rear sliding block 97 and the right rear sliding block 98 are driven to move along the rear side of the upper portion of the left nailing groove 87 and the rear side of the upper portion of the right nailing groove 88. Because the front and rear sides of the upper portion of the left nailing groove 87 and the front and rear sides of the upper portion of the right nailing groove 88 are all inclined planes, when the left front sliding block 95 and the right front sliding block 96 respectively move along the front side of the upper portion of the left nailing groove 87 and the front side of the upper portion of the right nailing groove 88 and the left rear sliding block 97 and the right rear sliding block 98 respectively move along the rear side of the upper portion of the left nailing groove 87 and the rear side of the upper portion of the right nailing groove 88, the gap between the left front sliding block 95 and the left rear sliding block 97 and the gap between the right front sliding block 96 and the right rear sliding block 98 both change.

A turning angle fixed plate 201, which is vertical to the left turning shaft 83, is fixed on the left bottom plate 81, and the turning angle fixed plate 201 has graduation reflecting the turning angle of the left guiding plate 85. An arc-shaped turning guiding slot 202, which is coaxial with the left turning shaft 83, is disposed on the turning angle fixed plate 201. A turning angle adjusting bolt 203 passes through the turning guiding slot 202 to connect to the left guiding plate 85. When the turning angle adjusting blot 203 is loosened, the left guiding plate 85 moves along the left turning shaft 83.

Figure 8:
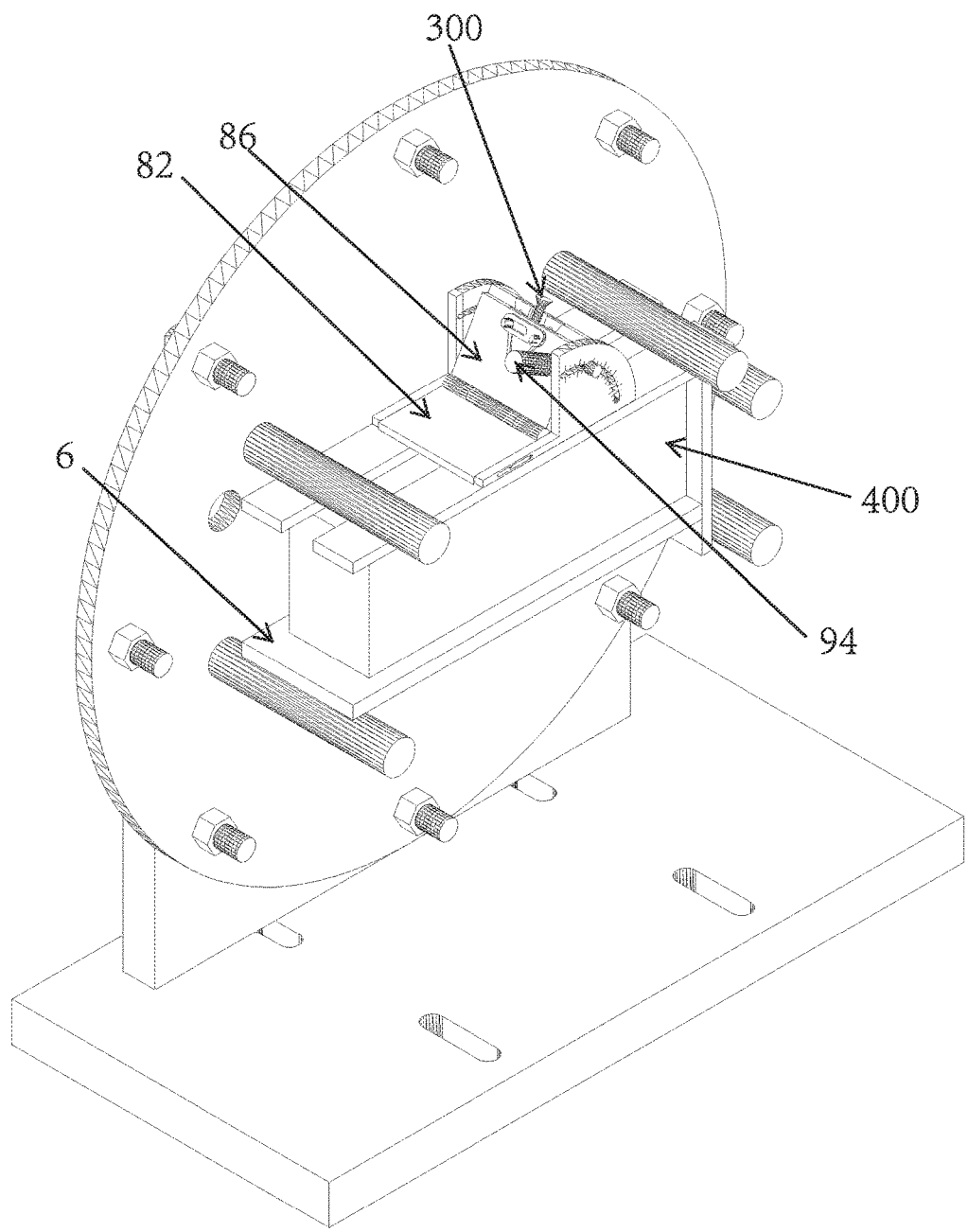
FIG. 8 is a schematic diagram illustrating that a test device of universal nail/screw holding power according to the present disclosure is in a penetrating state.
Figure 9:
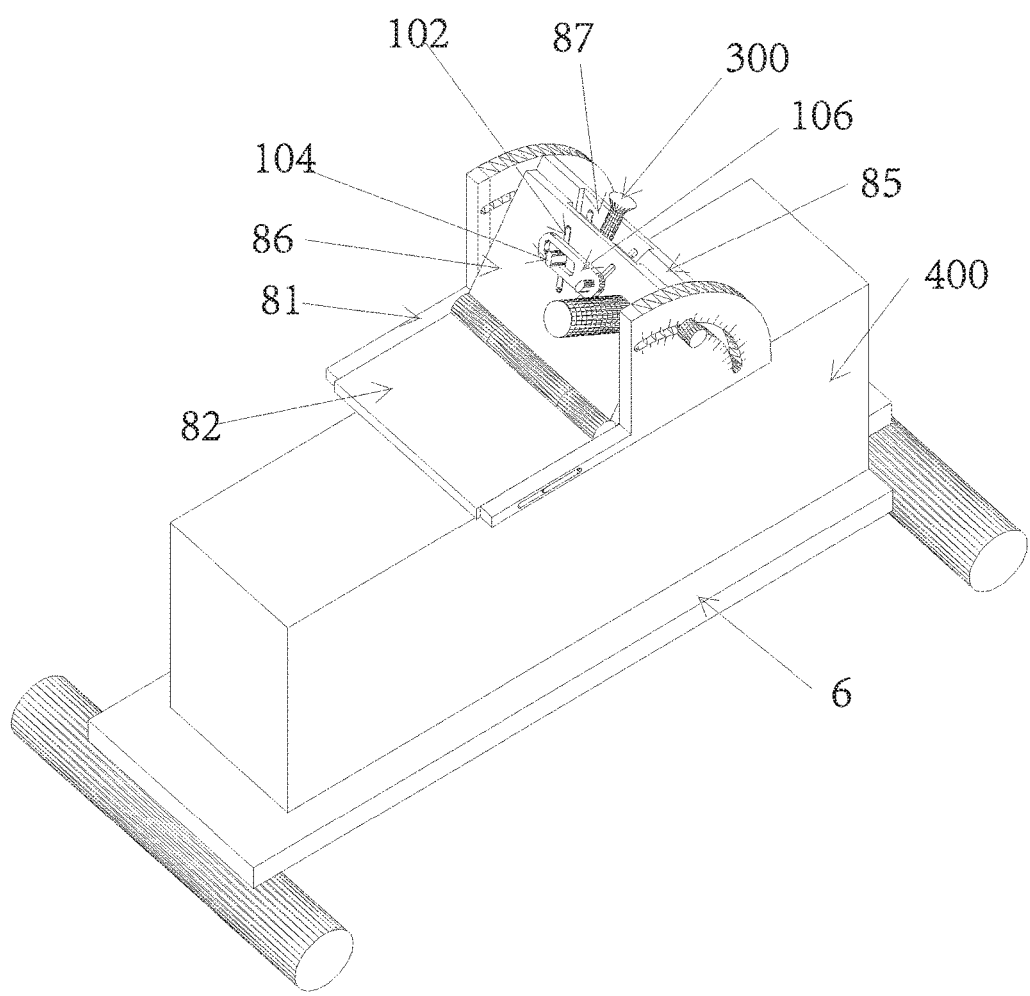
FIG. 9 is a schematic diagram illustrating that a penetrating guiding apparatus according to the present disclosure is in a penetrating state.
Figure 10:
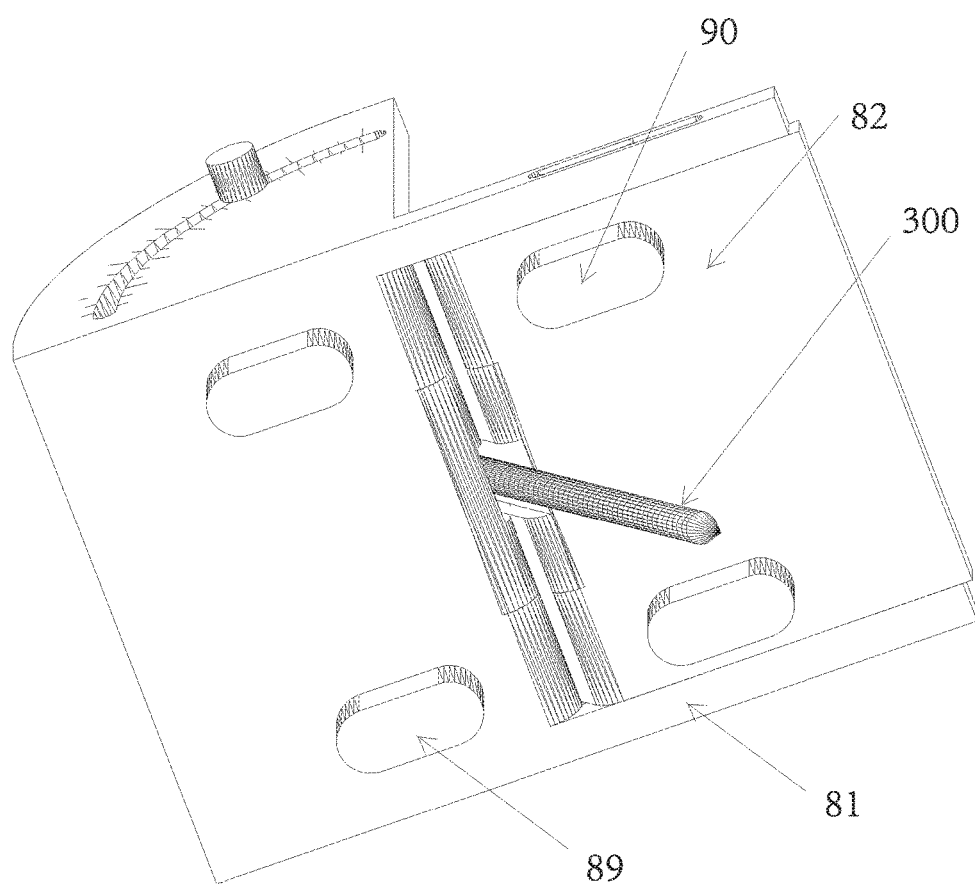
FIG. 10 is another diagram illustrating that a penetrating guiding apparatus according to the present disclosure is in a penetrating state.

Reference is made to FIG. 8 to FIG. 10. When penetrating a nail/screw 300 into a test piece 400, the test piece 400 such as wood is placed between the upper bearing plate 5 and the lower bearing plate 6, and the lower surface of the test piece 400 is in contact with the lower bearing plate 6. The trapezoid bolt 31 is tightened up to fix the disk 3 and the test piece 400, and the lower bearing plate 6 can bear the test piece 400 stably. Because the device provided by the present disclosure is disposed with the penetrating guiding apparatus 8, when penetrating, the disk 3 can be turned to any angle as long as an action force can be applied to the nail/screw 300. The penetrating process is as follows. The left guiding plate 85 is turned (overturned) by taking the left turning shaft 83 as the center to a desired angle, the turning angle adjusting bolt 203 is tightened up to avoid the left guiding plate 85 turning, then the right guiding plate 86 is turned (overturned) by taking the right turning shaft 84 as the center to an angle parallel to the left guiding plate 85; in the meantime, the connecting blot 94 is turned, the right bottom plate 82 moves with respect to the left bottom plate 81 to change the distance between the left guiding plate 85 and the right guiding plate 86 to enable the gap between the bottom surface of the left nailing groove 87 of the left guiding plate 85 and the bottom surface of the right nailing groove 88 of the right guiding plate 86 to be substantially the same as the diameter of the nail/screw 300; the front sliding rod 103 is adjusted to move in the left front sliding slot 99 and the right front sliding slot 100 to change the position of the left front sliding block 95 and the right front sliding block 96; in the meanwhile, the rear sliding rod 104 is adjusted to move in the left rear sliding slot 101, the right rear sliding slot 102 and the lateral guiding slot 200 to change the position of the left rear sliding block 97 and the right rear sliding block 98; because the left front sliding block 95, the right front sliding block 96, the left rear sliding block 97 and the right rear sliding block 98 are respectively disposed on the inclined front and rear sides of the left nailing groove 87 and the inclined front and rear sides of the right nailing groove 88, when the upper-and-lower position of the sliding blocks changes, the gap between the left front sliding block 95 and the left rear sliding block 97 and the gap between the right front sliding block 96 and the right rear sliding block 98 both change. When the gap is adjusted to be substantially the same as the diameter of the nail/screw 300, the nail/screw 300 passes through the gap between the left front sliding block 95 and the left rear sliding block 97 or passes through the gap between the right front sliding block 96 and the right rear sliding block 98; in the meanwhile, the nail/screw 300 passes through the gap between the bottom surface of the left nailing groove 87 of the left guiding plate 85 and the bottom surface of the right nailing groove 88 of the right guiding plate 86, and then passes through the through groove 51 disposed on the upper bearing plate 5 to be penetrated to the test piece 400 placed on the lower bearing plate 6. By means of the manner, when penetrating the nail/screw 300 into the test piece 400, the nail/screw 300 is guided by the bottom surface of the left nailing groove 87 of the left guiding plate 85 and the bottom surface of the right nailing groove 88 in the left-and-right direction, and is guided by the left front sliding block 95 and the left rear sliding block 97 or by the right front sliding block 96 and the right rear sliding block 98 in the front-and-rear direction, so that the penetrating process can be performed more accurately to ensure the penetrating directionality.

Figure 11:
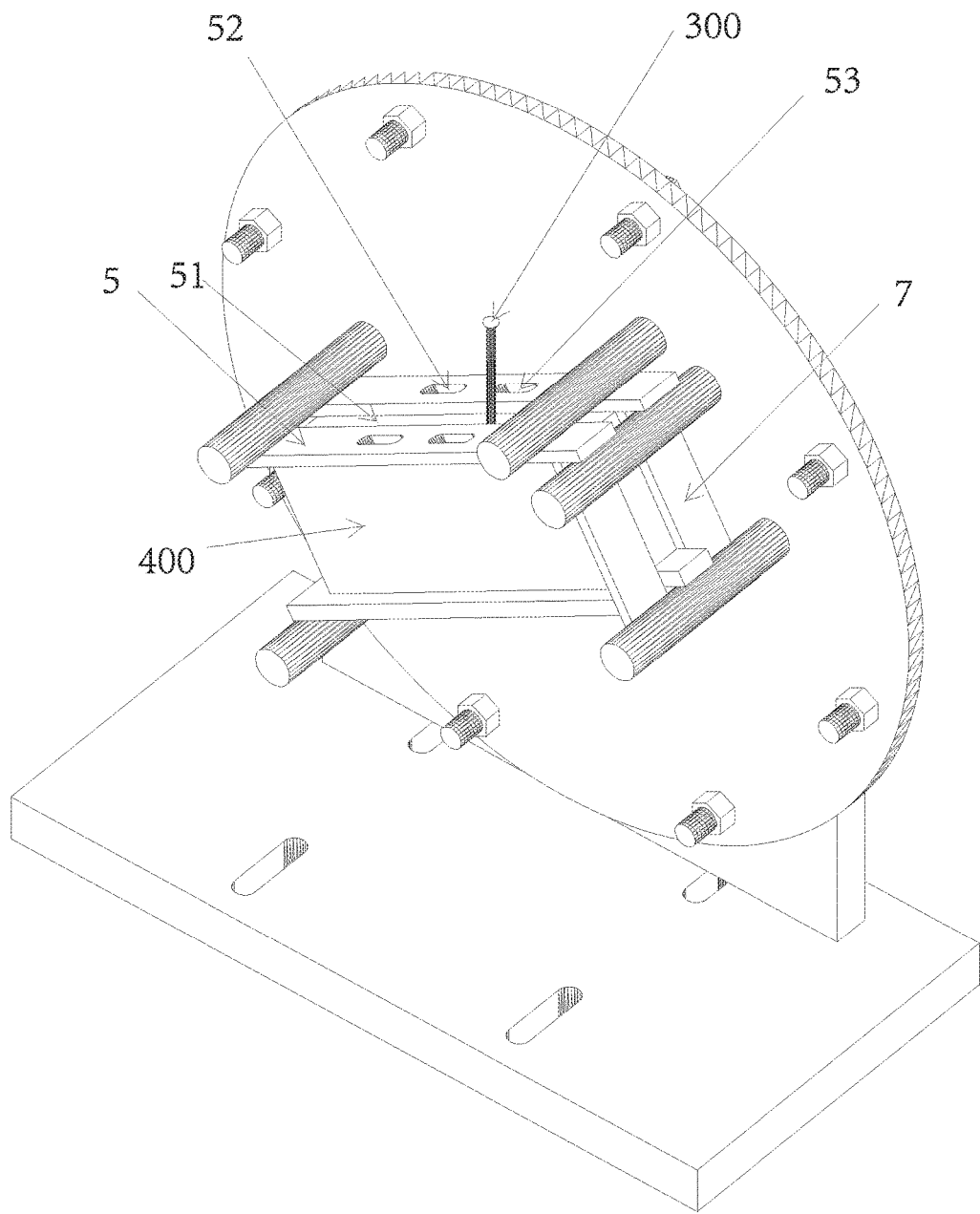
FIG. 11 is a schematic diagram illustrating that a test device of universal nail/screw holding power according to the present disclosure is in a nail/screw pulling-out state.

Reference is made to FIG. 10 and FIG. 11. When testing the nail/screw holding power applied to a test piece, for the purpose of convenience in operation, the penetrating guiding apparatus 8 is detached. When detaching the penetrating guiding apparatus 8, the penetrating guiding apparatus 8 is pulled upwards to separate the positioning platform 89 disposed on the left bottom plate 81 and the lower protrusion 90 disposed on the right bottom plate 82 from the positioning groove 52 and the guiding groove 53 disposed on the upper bearing plate 5. Alternatively, if a user intends keeping the penetrating guiding apparatus 8, the distance between the left guiding plate 85 and the right guiding plate 86 is enlarged, so that the nail/screw needed to be pulled out merely passes through the left guiding plate 85 and the right guiding plate 86 without contacting the left guiding plate 85 and the right guiding plate 86 or other components.

When pulling out the nail/screw, the upper surface of the test piece on which the nail/screw has been penetrated is in contact with the lower surface of the upper bearing plate 5, the nail/screw passes through the through groove 51 disposed on the upper bearing plate 5, and then the disk 3 is turned until the nail/screw on the test piece is in a vertically upward direction; the side of the test piece at which no nail/screw is penetrated is in contact with the side bearing plate 7, and the upper bearing plate 5 and the side bearing plate 7 together bear the test piece stably. After that, the trapezoid bolt 31 is tightened up to avoid the disk 3 and the test piece turning, so that the nail/screw can be pulled out upwards. As a result, the test device of universal nail/screw holding power provided by the present disclosure is capable of testing the nail/screw holding power of a nail/screw being penetrated at any angle. In addition, the present disclosure is simple in structure and convenient to use.

The above-mentioned descriptions represent merely the exemplary embodiment of the present disclosure, without any intention to limit the scope of the present disclosure thereto. Various equivalent changes, alterations or modifications based on the claims of the present disclosure are all consequently viewed as being embraced by the scope of the present disclosure.

What is claimed is:

1. A test device of universal nail/screw holding power, comprising:
   a base on which two opposite supporting plates are disposed, wherein two coaxial disks are respectively disposed on the two supporting plates, an upper bearing plate, a lower bearing plate, a side bearing plate located at one side of the upper bearing plate and the lower bearing plate are provided between the two disks, a through groove through which a nail/screw passes is provided on the upper bearing plate, a trapezoid slot which is concentric with the disk is provided on at least one supporting plate, and a plurality of trapezoid bolts are disposed along the same circumference on at least one disk; when the disk is turned, at least one trapezoid bolt is inserted into the trapezoid slot; when the at least one trapezoid bolt engages with the trapezoid slot and then is tightened up, the at least one trapezoid bolt and the trapezoid slot cooperatively limit the turn of the disk.

2. The test device of universal nail/screw holding power according to claim 1, wherein a penetrating guiding apparatus is provided, comprising a left bottom plate disposed on the upper surface of the upper bearing plate, a left guiding plate rotatably connected with the left bottom plate through a left turning shaft, a right guiding plate rotatably connected with a right bottom plate through a right turning shaft, wherein the left turning shaft and the right turning shaft are parallel to each other and the left guiding plate and the right guiding plate are relative to each other; a nailing groove formed on a relative surface of the left guiding plate and the right guiding plate, and the nailing groove communicated with the through groove; the right bottom plate slidably connected with the left bottom plate in a direction vertical to the right turning shaft; a position giving slot, which extends in a direction vertical to the left turning shaft, disposed on the left guiding plate, and a connecting bolt, which passes through the position giving slot, connected with the right guiding plate through screw threads; when turning the connecting bolt, the right bottom plate being pushed to slide with respect to the left bottom plate so as to change a distance between the left guiding plate and the right guiding plate which are relative and parallel to each other; a turning angle fixed plate, which is vertical to the left turning shaft, fixed on the left bottom plate, and an arc-shaped turning guiding slot, which is coaxial with the left turning shaft, disposed on the turning angle fixed plate, and a turning angle adjusting bolt passing through the turning guiding slot to connect to the left guiding plate.

3. The test device of universal nail/screw holding power according to claim 2, wherein the front and rear sides of an upper portion of the nailing groove are inclined planes and a width of the upper portion of the nailing groove is wide at top and narrow at bottom in the front-and-rear direction; two sliding blocks are oppositely and slidably disposed at the front and rear sides of the nailing groove; a front sliding slot and a rear sliding slot which are parallel to the front and rear sides of the nailing groove are disposed on the left guiding plate and the right guiding plate; a front sliding rod and a rear sliding rod respectively pass through a front sliding block, a front sliding slot, a rear sliding block and a rear sliding slot; the front sliding rod axially passes through a fore-and-aft gap controlling plate, the rear sliding rod axially passes through a lateral guiding slot disposed on the fore-and-aft gap controlling plate, and the lateral guiding slot parallelly extends along the axis of the left turning shaft; when the front sliding rod slides in the front sliding slot and the rear sliding rod slides in the rear sliding slot and the lateral guiding slot, a gap between the front sliding block and the rear sliding block changes.

4. The test device of universal nail/screw holding power according to claim 2, wherein a lower protrusion protruding downwards is provided at the bottom of the right bottom plate, and the lower protrusion is slidably cooperated with a guiding groove disposed on the upper bearing plate in a direction vertical to the right turning shaft.

5. The test device of universal nail/screw holding power according to claim 2, wherein a side protrusion extending forwards and backwards is respectively disposed at the front side and the rear side of the right bottom plate, and the side protrusion is slidably cooperated with a guiding sliding track disposed on the left bottom plate in a direction vertical to the right turning shaft.

6. The test device of universal nail/screw holding power according to claim 2, wherein the turning angle fixed plate has graduation reflecting the turning angle of the left guiding plate.

7. The test device of universal nail/screw holding power according to claim 1, wherein a plurality of connecting rods parallel to the axis of the disk are provided between the two disks, and the upper bearing plate, the lower bearing plate and the side bearing plate are fixed on the connecting rods.

8. The test device of universal nail/screw holding power according to claim 1, wherein the two supporting plates are movably connected to the base in a direction parallel to the axis of the disk with respect to the base.

\* \* \* \* \*